United States Patent
Spring et al.

(10) Patent No.: US 8,927,595 B2
(45) Date of Patent: Jan. 6, 2015

(54) TOPICAL AVERMECTIN FORMULATIONS AND METHODS FOR ELIMINATION AND PROPHYLAXIS OF SUSCEPTIBLE AND TREATMENT RESISTANT STRAINS OF HEAD LICE

(75) Inventors: Nicholas Spring, Horsham, PA (US); Garry T. Gwozdz, Bethlehem, PA (US)

(73) Assignee: Sanofi-Topaz, Inc., Wilmington, DE (US)

( * ) Notice: Subject to any disclaimer, the term of this patent is extended or adjusted under 35 U.S.C. 154(b) by 0 days.

(21) Appl. No.: 13/116,547

(22) Filed: May 26, 2011

(65) Prior Publication Data

US 2011/0275582 A1    Nov. 10, 2011

Related U.S. Application Data

(62) Division of application No. 11/871,660, filed on Oct. 12, 2007.

(60) Provisional application No. 60/851,352, filed on Oct. 12, 2006, provisional application No. 60/976,259, filed on Sep. 28, 2007.

(51) Int. Cl.
*A01N 43/90* (2006.01)
*A01N 25/04* (2006.01)
*A61P 33/00* (2006.01)
*A01N 25/02* (2006.01)
*A61K 31/7048* (2006.01)

(52) U.S. Cl.
CPC ............ *A01N 43/90* (2013.01); *A61K 31/7048* (2013.01)
USPC ......................................... 514/450; 504/363

(58) Field of Classification Search
None
See application file for complete search history.

(56) References Cited

U.S. PATENT DOCUMENTS

| | | |
|---|---|---|
| 4,199,569 A | 4/1980 | Chabala et al. |
| 5,929,086 A | 7/1999 | Watts |
| 5,952,372 A | 9/1999 | McDaniel |
| 6,006,758 A | 12/1999 | Thorne |
| 6,063,771 A | 5/2000 | Snyder |
| 6,103,248 A | 8/2000 | Burkhart et al. |

(Continued)

FOREIGN PATENT DOCUMENTS

| | | | |
|---|---|---|---|
| EP | 0179583 | 4/1986 | |
| EP | 1609460 | * 12/2005 | ............... A61K 7/48 |

(Continued)

OTHER PUBLICATIONS

Office Action mailed Oct. 28, 2010 in U.S. Appl. No. 12/115,291.

(Continued)

*Primary Examiner* — Rachael E Bredefeld
(74) *Attorney, Agent, or Firm* — Choate, Hall & Stewart LLP; Charles E. Lyon (57) ABSTRACT

An avermectin-based topical formulation is disclosed which is useful for prevention and treatment of head lice (*Pediculus humanus* capitis). This topical formulation may be formulated as a shampoo-condition which comprises an effective amount of avermectin, solubilizers, suspending agents, preservatives, non-ionic surfactants, humectants, a silicone compound, and water. Also disclosed are methods of using the topical formulations disclosed within this specification to treat either a susceptible or treatment-resistant strain of lice, as well as uses in the manufacture of a medicament for treating or preventing a lice infestation from a susceptible or treatment-resistant strain in a human patient.

41 Claims, 4 Drawing Sheets

22,23-dihydroavermectin B$_{1a}$ (Ivermectin B$_{1a}$)

(56) References Cited

U.S. PATENT DOCUMENTS

| | | | |
|---|---|---|---|
| 6,107,397 | A | 8/2000 | Blankenburg et al. |
| 6,262,031 | B1 | 7/2001 | Larouche et al. |
| 6,265,384 | B1 | 7/2001 | Pearlman |
| 6,319,945 | B1 | 11/2001 | Parks |
| 6,399,651 | B1 | 6/2002 | Parks |
| 6,399,652 | B1 | 6/2002 | Parks |
| 6,482,425 | B1 | 11/2002 | Huet et al. |
| 6,524,602 | B1 | 2/2003 | Burkhart et al. |
| 6,727,228 | B2 | 4/2004 | Janssen et al. |
| 6,927,210 | B1 | 8/2005 | Thompson et al. |
| 7,064,108 | B2 | 6/2006 | Guzzo et al. |
| 2003/0040504 | A1* | 2/2003 | Gans et al. ............. 514/72 |
| 2003/0180352 | A1 | 9/2003 | Patel et al. |
| 2003/0202997 | A1 | 10/2003 | Campbell et al. |
| 2004/0097377 | A1 | 5/2004 | Hahn et al. |
| 2004/0166183 | A1 | 8/2004 | Ruseler-van Embden et al. |
| 2004/0167084 | A1 | 8/2004 | Parks |
| 2005/0143325 | A1 | 6/2005 | Guzzo et al. |
| 2005/0220742 | A1 | 10/2005 | Breen |
| 2005/0276763 | A1 | 12/2005 | Pfeifer et al. |
| 2007/0020304 | A1 | 1/2007 | Tamarkin et al. |
| 2008/0214657 | A1 | 9/2008 | Spring et al. |
| 2008/0275107 | A1 | 11/2008 | Spring et al. |
| 2010/0093652 | A1 | 4/2010 | Spring et al. |

FOREIGN PATENT DOCUMENTS

| | | |
|---|---|---|
| FR | 2 854 074 A1 | 10/2004 |
| WO | WO-00/42990 A1 | 7/2000 |
| WO | WO-01/11964 A1 | 2/2001 |
| WO | WO 03/024223 | 3/2003 |
| WO | WO 2004/093886 | 11/2004 |
| WO | WO 2005/000241 | 1/2005 |
| WO | WO 2005/112950 | 12/2005 |
| WO | WO 2008/067054 | 6/2008 |
| WO | WO 2008/137699 | 11/2008 |
| WO | WO 2010/051348 | 5/2010 |

OTHER PUBLICATIONS

Crodalan AWS, "Solubilised acetylated lanolin alcohol derivative", *Croda Chemicals European Personal Care*, 2001.
Davis et al.,"Physico-chemical studies on aerosol solutions for drug delivery I. Water-propylene glycol systems", *International Journal of Pharmaceutics*, Elsevier, 1(2): 71-83, 1978.
HLB Systems, "HLB Systems; HLB values of some Surfactants", Internet Citation, Jul. 24, 2001, pp. 1-4; XP002557520.
Lide, "Viscosity of Liquids", CRC Handbook of Chemistry and Physics, 73$^{rd}$ Edition 1992-1993, pp. 6-167, 1992.
Weast, "Viscosity of Liquids", CRC Handbook of Chemistry and Physics, 66$^{th}$ Edition 1985-986, pp. F35-F42, 1985.
International Search Report for PCT/US07/081258, dated Aug. 19, 2008.
Extended European Search Report, Application No. EP08755014, dated Nov. 9, 2010.
Extended European Search Report, Application No. EP07871159, dated Nov. 15, 2010.
International Search Report dated Dec. 4, 2009.
Asenov et al., "Efficacy of chemical and botanical over-the-counter pediculicides available in Brazil, and off-label treatments, against head lice ex vivo", *International Journal of Dermatology*, 49: 324-330, 2010.
Final Office Action dated Aug. 17, 2009, U.S. Appl. No. 12/115,291.
Material Safety Data Sheets, "Diethylene Glycol Monomethyl Ether, Glycol Ether DM", pp. 1-4, 1999.
Cully et al., "Identification of a *Drosophila melanogaster* Glutamate-gated Chloride Channel Sensitive to the Antiparasitic Agent Avermectin", *The Journal of Biological Chemistry*, 271(33): 20187-20191, 1996.
Burkhart, et al., "Safety and efficacy of pediculicides for head lice", *Expert Opin. Drug Saf.*, 5(1): 169-179, 2006.
Downs, et al., "Evidence for double resistance to permethrin and malathion in head lice", *British Journal of Dermatology*, 41: 508-511, 1999.
Takano-Lee et al., "Home Remedies to Control Head Lice: Assessment of Home Remedies to Control the Human Head Louse, *Pediculus humanus capitis* (Anoplura: Pediculidae)", *Journal of Pediatric Nursing*, 19(6): 393-398, 2004.
Yang et al., Ovicidal and Adulticidal Activity of *Eucalyptus globulus* Leaf Oil Terpenoids against *Pediculus humanus capitis* (Anoplura: Pediculidae), *Journal of Agricultural and Food Chemistry*, 52: 2507-2511, 2004.
Yoon et al., "Resistance and cross-resistance to insecticides in human head lice from Florida and California", *Pesticide Biochemistry and Physiology*, 80: 192-201, 2004.
Burkhart, "Relationship of Treatment-Resistant Head Lice to the Safety and Efficacy of Pediculicides", *Mayo Clin. Proc.*, 79: 661-666, 2004.
Glaziou, et al., "Efficacy of ivermectin for the treatment of head lice (*Pediculosis capitis*)", *Tropical Medicine and Parasitology*, 45: 253-254, 1994.
Youssef, et al., "Topical Application of Ivermectin for Human Ectoparasites", *American Journal of Tropical Medicine and Hygiene*, 53(6): 652-653, 1995.
Dunne et al., "A field study of the effects of ivermectin on ectoparasites of man", *Transactions of the Royal Society of Tropical Medicine and Hygiene*, 85: 550-551, 1991.
Aldon Corporation, Material Safety Data Sheet for Coconut Oil, Avon, NY, 1996.
Office Action mailed Nov. 13, 2008 in U.S. Appl. No. 12/115,291.
Rowe et al., Handbook of Pharmaceutical Excipients 5th Edition, Pharmaceutical Press and the American Pharmactists Association: 83-85 (2006).
European Search Report for EP 09824117.7, 9 pages (Aug. 9, 2013).
Extended European Search Report for EP 13176927.5-1454, 9 pages (Sep. 25, 2013).
Cetaphil Moisturizing Lotion, Mintel Global New Products Database, 1-1 (2000).
Mumcuoglu et al., Systemic Activity of Ivermectin on the Human Body Louse, Journal of Medical Entomology, 27(1): 72-75 (1990).
International Search Report for PCT/US09/62500, 2 pages (mailed Dec. 15, 2009).

* cited by examiner

FIGURE 1A Avermectin $B_{1a}$

FIGURE 1B Avermectin $B_{1b}$

FIGURE 2A  22,23-dihydroavermectin $B_{1a}$ (Ivermectin $B_{1a}$)

FIGURE 2B  22,23-dihydroavermectin $B_{1b}$ (Ivermectin $B_{1b}$)

TOPICAL AVERMECTIN FORMULATIONS AND METHODS FOR ELIMINATION AND PROPHYLAXIS OF SUSCEPTIBLE AND TREATMENT RESISTANT STRAINS OF HEAD LICE

RELATED APPLICATIONS

This application is a divisional application of and claims priority to application Ser. No. 11/871,660, filed Oct. 12, 2007, currently pending; which claims the benefit under 35 U.S.C. §119(e) of U.S. patent application Ser. No. 60/851,352 filed Oct. 12, 2006 and U.S. patent application Ser. No. 60/976,259 filed Sep. 28, 2007, each of which are incorporated herein by reference in its entirety.

FIELD OF THE INVENTION

The present invention relates to topical formulations containing avermectin for use in the prophylactic and therapeutic treatment of a head lice infestation in humans. The topical formulations of the present invention are effective against both susceptible and treatment resistant strains of head lice. To this end, the present invention also relates to methods of treating an infestation of head lice which comprises administering one or multiple doses of the disclosed topical formulations to a human patient, wherein the infestation being treated represents a susceptible and/or treatment-resistant strain of head lice.

BACKGROUND OF THE INVENTION

Head lice, *Pediculus humanus* capitis, are parasitic insects that mainly live and feed in the scalp and neck hairs of human hosts. A typical infested scalp of a patient with head lice houses about 20 female lice, which are prolific egg layers over the course of their 30-day life cycle. These eggs are cemented to the hair shaft and are commonly called nits. Head lice have a similar appearance to wingless ants. Like all insects, the parasite has a body that is constructed of a hard chitinous exoskeleton. The egg case that surrounds the nits is of similar construction and is glued to the hair shaft via a cement that is similar in characteristics to the hair keratin itself. Infections, irritation and lesions to the scalp are common side effects of head lice infestation. Head lice infestation is an oft occurring problem in the United States and is easily spread from direct head-to-head contact with an infected person's hair and common usage of combs and clothing. There are between 6 to 12 million annual head lice infestations in the United States. Grade school children suffer most from head lice infestations, with one result being an accumulation of absences from school, where lice outbreaks are believed to account for 12 million to 24 million missed days a year. A majority of public schools have instituted a no lice or a no lice and no-nit policy, forcing absenteeism on children and maybe forcing working parents to stay at home to look after them. For a review, see Burkhart and Burkhart (2006, Expert Opin. Drug Saf. 5(1): 169-179).

Treatment for eliminating head lice traditionally included home remedies such as smearing mayonnaise, olive oil, a hair pomade, or some heavily viscous material about an infested scalp coupled with rigorous combing of the hair and meticulous removal of adult lice, nymphs, and nits. Though these home remedies do not kill head lice, the prevailing thought is that the viscosity of the material makes it hard for head lice to roam about the scalp, making for easy removal. Such home remedies are usually ineffective at controlling head lice due to the ability of the lice to revive rapidly once these materials are removed.

More effective treatments for eliminating head lice involve massaging the infested scalp with over-the-counter (OTC) topical creams containing active insecticides. Because of their potential toxicity to the human host, the use of these topical formulas are regulated by the FDA. Over-the-counter insecticides typically have pyrethrins or permethrin as active ingredients.

Pyrethrins are any one of six naturally occurring insecticides extracted from the chrysanthemum flower. Along with its synthetic derivative, permethrin, these molecules act on susceptible head lice by increasing sodium levels in the nervous system of the lice. The increased sodium levels cause membrane depolarization in the nervous system of the head lice, which eventually leads to spastic paralysis and death of the head lice.

When first introduced, both pyrethrin and permethrin were highly effective at eliminating susceptible lice. In the late 1980's, various formulations of both active ingredients had a high efficacy for eliminating adult head lice and their nits. However, recent reports indicate that treatment-resistant strains of head lice have evolved for Nix®, having 1% permethrin as an active ingredient, and various Rid® products, having approximately 0.33% pyrethrin as active ingredients. It comes as no surprise that strains of treatment-resistant head lice have been identified in both the United States and Europe due to the similar killing pathway for both insecticides.

Prescription products are also currently available and contain either lindane or malathion as the active ingredient. These insecticides specifically target the nervous system of the head lice. The chlorinated hydrocarbon, lindane, is formulated as a topical shampoo and is prescribed to treat head lice infestations. Lindane eliminates head lice by effectively slowing the insect's central nervous system causing paralysis and eventual death.

The reports of continued effectiveness of lindane for eliminating head lice is inconsistent at best. Reports on the efficacy of lindane for treating head lice have been listed from 17% in the U.S. to as high as 61% and 93% in other parts of the world. However, treating head lice with lindane poses problems for the human host. Side effects include toxicity to the central nervous system, convulsions, seizures; and it may be a carcinogen. Lindane has also been reported to have a slow killing time, and has poor ovicidal capacities.

Malathion is also available as a prescription insecticide to treat head lice infestations (e.g., OVIDE® an alcohol based lotion containing 0.5% malathion, terpeneol, dipentene and pine needle oil in 78% isopropyl alcohol). It is an organophospate that causes spastic paralysis and death in head lice.

As noted above, recently there has been an increase in strains of head lice which show resistance to available OTC and prescription treatments for head lice infestation. These parasites have adapted to chemical treatments using pyrethrins, permethrins, lindane, and malathion. In the US, permethrin resistant lice have been found in Massachusetts, Idaho, Texas, California and Florida. Single and dual resistance to pyrethrins/permethrins and malathion has been broadly reported in Great Britain (see Downs et al., 1999, *Br. J. Dermatology* 141:508-511).

Strains of head lice have been identified worldwide which are resistant to all currently available topical treatments. Possible neural damage to the human host prevents raising the insecticide levels above the current threshold in an attempt to combat these newer treatment-resistant head lice. One possible way to address this alarming increase in treatment resistant head lice would be to develop and introduce a topical pediculicide formulation which is (i) safe; (ii) effective against head lice infestation from both susceptible and treatment-resistant strains; (iii) is convenient for patient use; and, (iv) has not previously been marketed for such an indication. Such a strategy is disclosed herein by utilizing an anthelmintic agents derived from avermectin.

Avermectin is a natural fermentation product derived from the soil bacterium *Streptomyces avermitilis*. Avermectin naturally occurs as abamectin, a mixture of avermectin isomers containing >80% avermectin $B_{1a}$ and <20% avermectin $B_{1b}$, see FIGS. 1A and 1B, respectively. Other semi-synthetic forms of avermectin and mutated forms of *Streptomyces avermitilis* containing avermectin, for example doramectin, ivermectin, selamectin, and eprinomectin have found medicinal uses as well.

Ivermectin is the synthetic dihydro form of avermectin and is an effective insecticide. These compounds have been shown to selectively bind with high affinity to glutamate-gated chloride ion channels (GluCl channels) as well as γ-aminobutyric acid (GABA) receptors, thus blocking the chemical transmission across the nerve synapses which utilize glutamate and GABA, respectively. This blockage, which occurs in invertebrate nerve and muscle cells, leads to an increase in the permeability of the cell membrane to chloride ions with hyperpolarization of the nerve or muscle cell, resulting in paralysis and death of the parasite.

The selectivity of ivermectin is attributable to the fact that some mammals do not have glutamate gated chloride channels and that the compound has a low affinity for mammalian ligand-gated chloride channels. In addition, ivermectin does not readily cross the blood brain barrier in humans. Thus, ivermectin has a documented history of highly safe and efficacious use in humans and animals. For example, over 400 million doses of orally formulated ivermectin have been used for controlling river blindness since 1986.

Ivermectin is commercially available as STROMECTOL® for eradication of *Strongyloides stercoralis*, which causes strongyloidiasis, and *Onchocerca volvulus*, which causes onchocerciasis. Ivermectin is also available as MECTIZAN® for eradication of *Onchocerca volvulus* and *Wuchereria bancrofti*. Ivermectin is usually available as a mixture containing at least 90% 5-O-demethyl-22,23-dihydroavermectin $A_{1a}$ and less than 10% 5-O-demethyl-25-de(1-methylpropyl)-22, 23-dihyro-25-(1-methylethyl) avermectin $A_{1a}$, generally referred to as 22,23-dihydroavermectin $B_{1a}$ and $B_{1b}$, or $H_2B_{1a}$ and $H_2 B_{1b}$, respectively, see FIG. 2A and FIG. 2B respectively.

Glaziou et al. (1994, *Trop. Med. Parasitol.* 45: 253-254) disclose treating humans with a single oral 200 ug/kg dose (n=26). Oral ivermectin was effective at this concentration against head lice. A second dose was suggested for prophylaxis, but not as part of the initial therapeutic regime.

Youssef et al. (1995, *Amer. J. Trop. Med. Hyg.* 53(6):652-653) describe a method of topical application of ivermectin to treat head lice.

Dunne et al. (1991, *Trans. R. Soc. Trop. Med. Hyg.* 85: 550-551) disclose results from a study wherein ivermectin was administered as a single oral dose of 100-200 ug/kg to treat head lice infestation. Positive, but not absolute, results where reported for this oral dosing regime.

U.S. Pat. No. 4,199,569, issued Apr. 23, 1980, discloses ivermectin, which as noted above is a semisynthetic, anthelmintic agent derived from the avermectins, a class of highly active broad-spectrum anti-parasitic agents isolated from the fermentation products of *Streptomyces avermitilis*.

U.S. Pat. No. 6,103,248, issued to Burkhart and Burkhart, disclose a topical formulation for the treatment of head lice which includes a killing agent, and a lipophilic carrier having a viscosity within a range of from about 10,000 centipoise to about 85,000 centipoise at 21° C.

U.S. Pat. No. 6,524,602, also issued to Burkhart and Burkhart, disclose a topical formulation which includes a parasiticide and N,O-carboxymethyl-chitosan polymer, and a vehicle for the parasiticide and polymer.

U.S. Pat. No. 7,064,108, issued to Guzzo, et al., discloses an ivermectin-based topical gel composition comprising a pharmaceutically acceptable alcohol (30-40%; e.g., propylene glycol), a pharmaceutically acceptable glycol (30-40%; e.g., ethyl alcohol), and a pharmaceutically acceptable carrier. Ivermectin is contemplated at a w/v basis from 0.005 to 1.0%. Additional additives may include d-limonene, a non-ionic surfactant and a pharmaceutically acceptable viscosifying agent (e.g., hydroxypropylcellulose).

U.S. Pat. No. 5,952,372, issued to William McDaniel, discloses methods of treating rosacea in humans involving orally-administered or topically-applied ivermectin. The topical aspect of the invention suggests a topical formulation with about 2% ivermectin.

U.S. Pat. Nos. 6,399,652; 6,399,651 and 6,319,945, issued to L. Dean Parks, disclose methods of treating skin disorders via application of topical formulations containing ivermectin to treat acne vulgaris (the '652 patent), a variety of dermatoses (e.g., transient acantholytic dermatitis, acne miliaris necrotica, acne varioliformis, perioral dermatitis, and acneiform eruptions; the '651 patent) and seborrheic dermatitis (the '945 patent).

U.S. Pat. No. 6,262,031, issued to Larouche, et al. discloses an oral formulation of ivermectin to treat a head lice infestation.

It is evident that the OTC or prescription products presently available to the public for treatment or prevention of head lice each have their own significant drawbacks. Over-the-counter products such as pyrethrin and permethrin are presently compromised due to emerging strains of treatment-resistant head lice. On the other hand, the prescription products such as lindane and malathion carry recognized health risks and are also losing effectiveness due to the emergence of treatment-resistant lice. To this end, there remains a need for a patient friendly product that is safe and effective in treating susceptible and/or treatment-resistant head lice. The present invention addresses and meets this needs by disclosing an avermectin-based topical formulation and exemplifying an ivermectin-based topical formulation, and associated methods of use, which is safe, will appeal to the patient for ease of use and is shown to be effective against multiple strains of either susceptible and treatment-resistant head lice.

SUMMARY OF THE INVENTION

The present invention relates to a topical formulation for use in the prophylaxis or elimination of head lice (*Pediculus humanus* capitis) on a human host, wherein the formulation comprises a pharmaceutically effective amount of an avermectin compound, solubilizers, suspending agents, preservatives, non-ionic surfactants, humectants, and water.

The present invention also relates to a topical formulation for use in the prophylaxis or elimination of head lice (*Pediculus humanus* capitis) on a human host, wherein the formulation comprises a pharmaceutically effective amount of ivermectin, solubilizers, suspending agents, preservatives, non-ionic surfactants, humectants, and water.

In additional embodiments of the present invention, the topical avermectin/ivermectin-containing formulation may further comprise additional beneficial agents; non-limiting examples being nutrients and vitamins, and the absence of pharmaceutically accepted glycols.

The present invention relates to a method of treating a head lice infestation in a human patient which comprises topically administering to the patient an avermectin- or ivermectin-based formulation via one or multiple doses; the strain of head lice being either a susceptible strain, a treatment-resistant strain, or any combination of either or both types of strains within a specific human infestation.

The present invention also relates to a method of treating a head lice infestation in a human patient which comprises topically administering to the patient an avermectin- or an ivermectin-based formulation as disclosed herein by one dose or multiple doses; the strain of head lice being either a susceptible strain or a treatment-resistant strain or any combination of either or both types of strains within a specific human infestation.

Another aspect of the present invention relates to the use, in manufacture of a topical medicament for treating or preventing a head lice infestation from a treatment-resistant strain in a human patient, of avermectin or ivermectin.

Another aspect of the present invention relates to the use, in the manufacture of a medicament for treating or preventing a head lice infestation from a susceptible or treatment-resistant strain in a human patient, of a topical formulation according to the present invention.

The present invention further relates to a method of preventing a head lice infestation in a human patient at risk which comprises topically administering to the human an avermectin- or an ivermectin-based formulation as disclosed herein by one dose or multiple doses (preferably a single application) so as to prevent infestation in the patient at risk (i.e., a human likely to be in close contact with an infected individual) to a strain of head lice being either a susceptible strain or a treatment-resistant strain or any combination of either or both types of strains within a specific human infestation.

Therefore, the present invention relates to a method of eliminating or preventing an infestation of head lice on a human patient, whether the infecting head lice strain be a susceptible strain or a treatment resistant strain, which comprises applying one or multiple doses (applications) of the topical avermectin-containing formulation, including but not limited to an exemplified ivermectin-containing formulation, to the individual for a length of time to allow biologically effective contact between the active ingredient and the lice.

The present invention also relates to an avermectin- or ivermectin-based formulations which is effective against pediculosis via pubic lice (*Phthirus pubis*) and body lice (*Pediculus humanis* corporis). The formulations of the present invention may be used 'as is' to treat a pubic lice and/or body lice infestation, or may be altered to provide for a formulation with the consistency of a cream rinse or lotion that may be applied to the affected area(s), left on for a period of time as contemplated herein for treatment of head lice, and then rinsed off. Multiple dosing may also occur as contemplated herein for treating head lice with a formulation as disclosed herein.

Another aspect of the present invention relates to the use, in manufacture of a topical medicament for treating or preventing a pubic lice or body lice infestation from a treatment-resistant strain in a human patient, of avermectin or ivermectin.

Another aspect of the present invention relates to the use, in the manufacture of a medicament for treating or preventing a pubic lice or body lice infestation from a susceptible or treatment-resistant strain in a human patient, of a topical formulation according to the present invention.

DETAILED DESCRIPTION OF THE INVENTION

The present invention relates to an avermectin-containing topical formulation useful as a pediculicidal agent in the treatment or prevention of an infestation of head lice, where the infested lice may be either a susceptible or treatment-resistant strain of *Pediculus humanus* capitis.

One embodiment of the present invention relates to an ivermectin-containing topical formulation useful as a pediculicidal agent in the treatment or prevention of an infestation of head lice, particularly where the infested lice may be either a susceptible or treatment-resistant strain of *Pediculus humanus* capitis.

The avermectin/ivermectin-based formulations of the present invention address the emerging problem of treatment-resistant head lice strains by allowing use of a single product which is active in eliminating or preventing head lice infestations, whether the infestation represents a susceptible or treatment-resistant strain of head lice.

A portion of the current invention is exemplified by an ivermectin-based formulation in an assay to determine killing ability against permethrin-resistant head lice. It is well known in the art that similar treatment regimes are presently utilized to treat not only a head lice infestation, but also at least an infestation of pubic lice or body lice. Thus, it will be evident that avermectin- or ivermectin-based formulations will be effective in treating not only head lice, but also infestations of the human body of pubic lice and body lice. Pubic lice (*Phthirus pubis*, e.g., "crabs") are usually found in the pubic area but may also be found on facial hair, on eyelashes, on eyebrows, in the armpits, on chest hair, and, rarely, on the scalp.

Body lice (*Pediculus humanis* corporis) live and lay eggs in the seams of clothing. The lice are only present on the body when they feed. Under some conditions, these lice may transmit diseases such as typhus, relapsing fever, and trench fever. The formulations of the present invention may be used 'as is' to treat a pubic lice and/or body lice infestation. Of course, the core components of the disclosed formulation may be altered to provide for a formulation with the consistency of a cream rinse or lotion that may be applied to the affected area(s), left on for a period of time as contemplated for treatment of head lice, and then rinsed off. Multiple dosing may also occur as contemplated herein for treating head lice with a formulation as disclosed herein.

The present invention also relates to a method of treating or preventing a head lice infestation, whether the infestation be from a strain of head lice that remains susceptible to current OTC and prescription pediculicides ("a susceptible strain") or from a strain that is resistant to one or more available OTC and/or prescription formulations ("a treatment-resistant" or "drug-resistant" strain). Thus, one aspect of the invention relates to a method of treatment or prevention of an infestation of head lice on a human patient utilizing an avermectin- or ivermectin-based formulation, whether the infecting head lice strain may be a susceptible strain or a treatment-resistant strain.

This methodology comprises applying one dose or multiple doses (applications) of the topical avermectin- or ivermectin-containing formulation to the individual for a length of time to allow an effective amount of the active ingredient to contact the infecting lice.

An additional aspect of this portion of the invention relates to a method for prophylaxis or elimination of either susceptible or treatment-resistant head lice using the avermectin-containing formulation as a shampoo-conditioner, where the shampoo-conditioner is used twice during about a seven day period (day 1 and day 7), left on the scalp for 1 to 60 minutes at each application, and then rinsed with warm water. The shampoo-conditioner is formulated to leave the hair in good condition while ridding the scalp of lice.

Thus, another aspect of the present invention relates to the use, in manufacture of a topical medicament for treating or preventing a head lice, pubic lice or body lice infestation from a treatment-resistant strain in a human patient, of avermectin or ivermectin. Another aspect of the present invention relates to the use, in the manufacture of a medicament for treating or preventing a pubic lice or body lice infestation from a susceptible or treatment-resistant strain in a human patient, of a topical formulation according to the various formulations disclosed herein.

One central aspect of the present invention is that the topical formulation will comprise avermectin. Avermectin may be present at varying concentrations, with an expected range (at a weight/volume percentage) of from 0.005% to 5.0% (w/v) [i.e., a 1% avermectin formulation would include 1 gram (g) avermectin per 100 milliliters (ml) (1 g/100 ml)] of formulation volume.

Another contemplated range for an avermectin concentration would be from about 0.1% to about 2.0% (w/v), which is further supported in Example 1, where avermectin, in the form of ivermectin, concentrations of 0.25%, 0.5% and 1.0% were shown to promote effective killing of a permethrin-resistant strain of head lice.

Of course, dosing may be varied either by the altering the avermectin concentration, as noted above, or by increasing the amount of topical formulation applied to the scalp of the human patient. It will be evident upon review of this specification, that while an ivermectin-based formulation is exemplified herein, other known avermectins beside ivermectin are also contemplated as the active ingredient which will be useful to practice the present invention.

While dosing ranges may vary, it is expected that a single application (dosage) of an exemplified ivermectin-containing formulation of the present invention would be in the range from about 1 ml to about 100 ml; with an additional range being from about 3 ml to about 75 ml.

In a single embodiment, at least about 60 ml the topical formulation is applied to totally saturate the roots and to effectively cover the entire scalp area. It is evident upon review of this specification that the artisan may vary the ivermectin concentration and/or volume of the topical formulation to manipulate the effective amount of ivermectin to be delivered to the patient's scalp.

Another aspect of the present invention, as noted above, relates to multiple doses of the topical avermectin- or ivermectin-based formulations of the present invention. Multiple applications will include at least one, two, three or four additional dosages beyond the initial dose, with one or possibly two additional doses being most reasonably contemplated.

The initial dose is most likely in response to an infestation of head lice, while the additional subsequent dose(s) are follow up applications to eradicate lice that hatch following the first dose or lice that have somehow survived the first dosing. Multiple dosing for a therapeutic regime provides an opportunity to deliver greater amounts of avermectin spaced over a determined time frame.

One aspect of this portion of the invention relates to a method for prophylaxis or elimination of either susceptible or treatment-resistant head lice using the avermectin- or ivermectin containing formulation as a shampoo-conditioner. The shampoo-conditioner may be used twice during about a seven day period (day 1 and between about day 5 and day 9), as well as three or four times (with an initial application on day 1 followed for a second, third or fourth application at intervals from about 5 days to about 9 days). At each dosing, the formulation remains in the scalp for from about 1 minute to 60 minutes or from about 3 minutes to about 60 minutes, then rinsed with warm water.

The shampoo-conditioner is formulated to leave the hair in good condition while ridding the scalp of lice. Therefore, the present invention relates to a method of treating a head lice infestation in a human patient which comprises topically administering to the human a formulation as disclosed herein by one dose or multiple doses; the strain of head lice being either a susceptible strain or a treatment-resistant strain.

Furthermore, the present invention relates to a method of preventing a head lice infestation in a human patient at risk which comprises topically administering to the human a formulation as disclosed herein by one dose or multiple doses (preferably a single application) so as to prevent infestation in the patient at risk to a strain of head lice being either a susceptible strain or a treatment-resistant strain. Thus, methods of the present invention are useful for preventing head lice infestation in a human susceptible to such infestation.

Such an at risk individual would be a human coming into close contact with an infested individual, such as a family member or possibly in response to an outbreak within a confined space such as school or the workplace. Either a single or multiple dosing regime will be effective, the course of a prophylactic treatment most likely determined by the severity of the outbreak.

Thus, the present invention provides a formula for prophylaxis and elimination of head lice comprising an effective amount of ivermectin in a shampoo-conditioner. However, the formula may be delivered in various forms, non-limiting examples being creams, gels, pomades, and the like. The invention also provides a method for prophylaxis and elimination of head lice on human hosts comprising topically massaging said formula in a suitable carrier onto and about the infected area.

For the purposes of this invention, the following non-limiting definitions are used:

The term "active ingredient", when directed toward the present invention, refers to an avermectin, including but not limited its synthetic derivative, ivermectin. Ivermectin may be utilized as a mixture of over 80% 22,23-dihydroavermectin $B_{1a}$ and less than 20% 22,23-dihydroavermectin $B_{1b}$. As exemplified herein, ivermectin is a mixture of at least 90% 22,23-dihydroavermectin $B_{1a}$ and less than 10% 22,23-dihydroavermectin $B_{1b}$.

The terms "solubilizer" and/or "solubilizer phase" refers to compound or mixture of compounds in which the ivermectin is initially dissolved. The solubilizer phase is preferably a mixture of water miscible organic compounds. By way of example, solubilizers may include the surfactants polysorbate 80 and cetyl acetate or other surfactants as more fully described herein.

The term "suspending agent(s)" refers to organic compounds that suspend the pre-dissolved ivermectin before being dispersed in water. Suspending agents include, without limitation, olive oil, shea butter, coco butter, vegetable oil, and the like.

The term "preservative(s)" refers to compounds that reduce the growth of fungus and other bacterial agents. In one embodiment, preservatives are selected from the compounds in the paraben family.

The term "non-ionic surfactant(s)" refers to compounds which act at the water-air and water-oil interfaces, thereby enhancing wetting ability, emulsion stabilization, foaming, rheology, antistatic, lubricity, and surface conditioning properties of the shampoo-conditioner.

The term "emollient(s)" refers to compounds that soften and makes the skin smooth by preventing skin from loosing moisture.

The term "silicone compound" refers to hair conditioning agents that change the texture, feel, and appearance of human hair. In one embodiment, the silicone compound is cyclomethicone.

The term "susceptible" or "susceptible strain" refers to a strain of head lice which is susceptible to one or more available OTC and/or prescription pediculicides, having active ingredients selected from the group consisting of pyrethrins, permethrins, lindane, and malathion where the active ingredient is at least at the pharmaceutically acceptable treatment concentration allowable for that respective pediculicide(s) and all or effectively all head lice are killed at that concentration. In other words, a susceptible strain is a strain which will be effectively controlled following treatment with a pharmaceutically acceptable concentration for that respective pediculicide.

The term "treatment-resistant" or "drug-resistant" or any such similar term refers to a strain of head lice which shows resistance to one or more available OTC and/or prescription pediculicides having active ingredients selected from the group including, but not limited to one or more pyrethrins, permethrin, lindane, and malathion, where the active ingredient is at least at the pharmaceutically acceptable treatment concentration recommended or allowed for that respective pediculicide(s) and at least some head lice survive at that concentration. Pyrethrins which are approved for use on humans are extracted from the chrysanthum flower, of which there are six active constituents which are esters of two carboxylic acids (chrysanthemic acid and pyrethric acid) and four cyclopentenoles (pyrethrolone, cinerolone, and jasmolone I and II). So, it is evident that a treatment-resistant strain of lice is a strain that shows a measurable level of resistance to killing by a specific pediculicide treatment regime as compared to a susceptible strain, where all or effectively all of the head lice will be killed. Such a measure may be made by an art-accepted assay, for example, as disclosed herein in Example section 1; or may possibly be determined by other means (e.g., comparative testing in individuals).

The present invention is exemplified by, but in no way limited to, a topical ivermectin-containing formulation as disclosed in Table 1. This final formulation is in the consistency of a shampoo-condition and at least comprises an effective amount of ivermectin, as well as a solubilising agent(s), water, a suspending agent(s), a surfactant(s), silicone compound(s), and a preservative(s), in any combination and/or concentration which may be contemplated by the artisan upon review of this specification.

Solubilising Active Ingredient

Figure 1A:
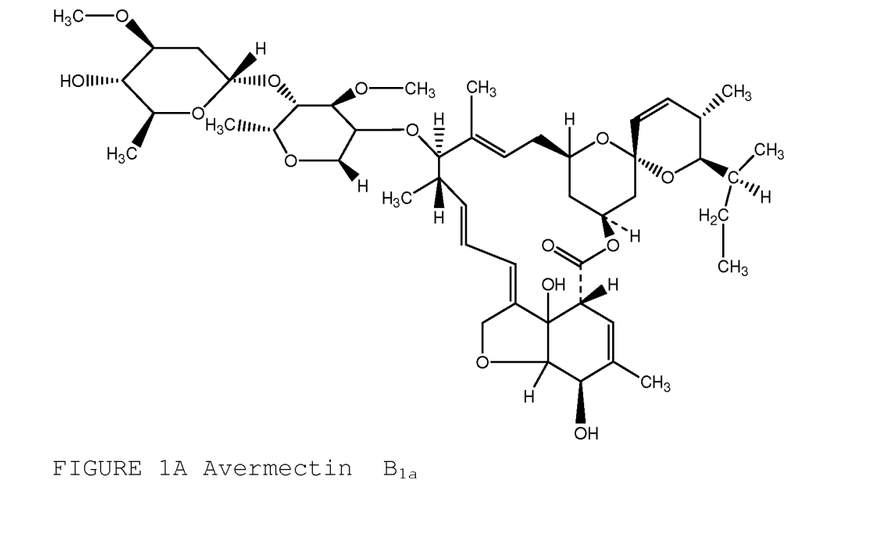
FIGS. 1A and 1B show the chemical structures of avermectin, form $B_{1a}$ (1A) and $B_{1b}$ (1B).
Figure 1B:
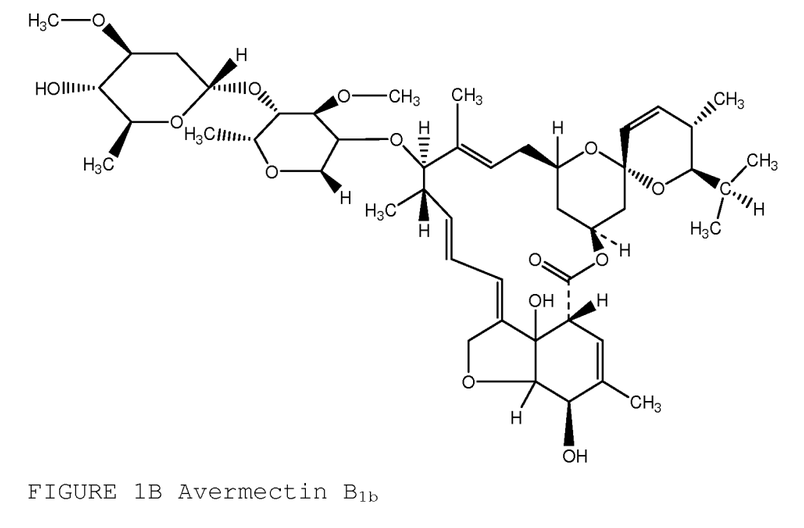
Figure 2A:
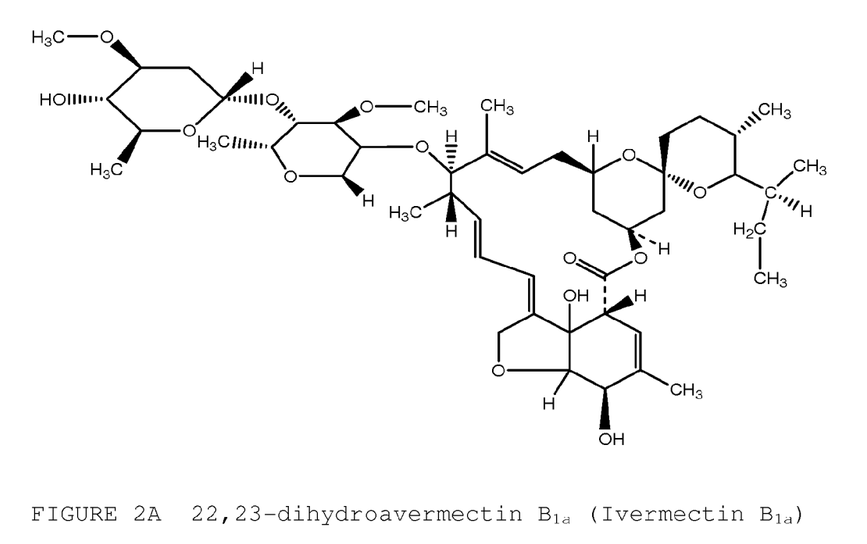
FIGS. 2A and 2B show the chemical structure for ivermectin, form $B_{1a}$ (2A) and $B_{1b}$ (2B).
Figure 2B:
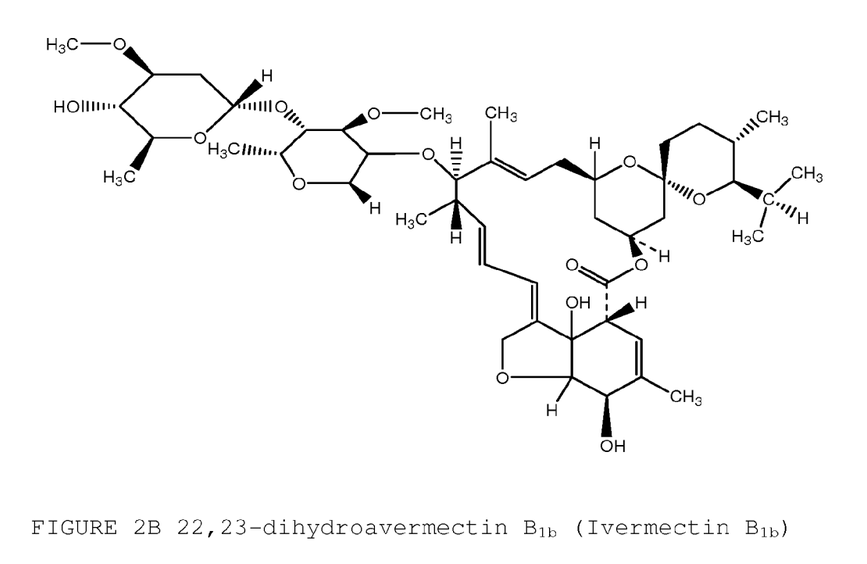

FIGS. 1A and 1B show the chemical formula for avermectin, forms $B_{1a}$ and $B_{1b}$. FIGS. 2A and 2B show ivermectin as a mixture comprising about 90% 22,23-dihydroavermectin $B_{1a}$ and less than about 10% 22,23-dihydroavermectin $B_{1b}$. Ivermectin may be delivered to a head lice infested scalp by way of an emulsion based shampoo-conditioner. However, ivermectin is hydrophobic and is poorly solvated by water. Thus, the active ingredient should preferably be pre-dissolved in suitable surfactants to improve the stability of said active ingredients in water. Preferably, these surfactants are easily soluble in water or are water miscible.

In one embodiment, ivermectin is pre-dissolved in a mixture containing the water miscible organic compounds, e.g. polysorbate 80, cetyl acetate, and acetylated lanolin alcohol. More specifically, ivermectin is present in the formula at a level of about 0.05% to 5%, or alternatively from about 0.1% to 2% by weight, or alternatively from about 0.25% to 1% by weight. Polysorbate 80 is present in the formula at a level of about 5% to about 25% by weight, or alternatively from about 10% to 15% by weight (e.g. about 11.25% to 13.5% by weight). Cetyl acetate is present in the formula at a level of about 0.5% to 10% by weight, or alternatively from about 1% to 4% by weight (e.g. about 1.50% to 3.75% by weight). Acetylated lanolin alcohol is present in the formula at a level of about 0.10% to 3% by weight, or alternatively from about 0.5% to about 1% by weight (e.g., 0.15% to 0.75% by weight).

Having these surface active agents bound to the surfaces of ivermectin will ensure that the active ingredient will be stable in the aqueous environment of the shampoo-conditioner. In one embodiment of the invention ivermectin may be stabilized by pharmaceutically accepted glycols present in said formula at a level below 30% by weight, such as, for example, below 25%, or below 20% or below 15% or below 10% or below 5%. In another embodiment of the invention said formula does not include any glycols.

Suspending Agents

Once the active ingredient is dissolved in a surfactant bath, ivermectin is placed in suspending agents. In one embodiment, a combination of fatty oils and fats serve as suspending agents. Olive oil is a triacylglyceride, where three fatty acids are tethered to a glycerol backbone and shea butter is primarily made of palmitic, stearic, oleic, linoleic, and arachidic fatty acids. Although these fatty acids have shown to be adequate home remedies for removal of head lice from the scalp, they do not kill head lice. Both olive oil and shea butter are viscous materials that slow the movement of adult lice to better remove them. Also note that both fatty acids can act as skin moisturizers. In one embodiment, olive oil is present in the formula at a level of about 20% to 30% by weight, or alternatively from about 25% to 28% by weight (e.g., about 27.5% by weight). Shea butter is present in the formula at a level of about 1% to 5% by weight (e.g. about 2% by weight). Other known suspending agents which may be utilized in the formulations and related methods include, but are not limited to, coconut oil, palm oil, cottonseed oil, vegetable oil, soybean oil, olive oil, peanut oil, corn oil, sunflower oil, safflower oil, jojoba oil, canola oil, shea butter, cocoa butter, milk fat, amaranth oil, apricot oil, argan oil, avocado oil, babassu oil, ben oil, algaroba oil, coriander seed oil, false flax oil, grape seed oil, hemp oil, kapok seed oil, meadowfoam seed oil, okra seed oil, perilla seed oil, poppyseed oil, prune kernel oil, pumpkin seed oil, quinoa oil ramtil oil, rice bran oil, camellia oil, thistle oil, wheat germ oil and combinations thereof.

Surfactants

The formulation may be further stabilized by non-ionic surfactants. In one embodiment of the invention, a fatty alcohol or a mixture of fatty alcohols serve as surfactants. Apart from additional stabilization of ivermectin, the non-ionic surfactants have various purposes in the surface chemistry of said formula, where said formula is used in a final product comprising a shampoo-conditioner. In addition to their surface-active properties, fatty alcohols are emollients that make the skin smoother and act at the water-air and water-oil interfaces, thereby enhancing wetting ability, emulsion stabilization, foaming, rheology, antistatic, lubricity, and surface conditioning properties of the formula. Suitable non-ionic surfactants include, without limitations, oleyl alcohol, lanolin alcohol, sorbitan tristearate, bees wax, erucyl alcohol, ricinolyl alcohol, arachidyl alcohol, capryl alcohol, capric alcohol, behenyl alcohol, lauryl alcohol, myristyl alcohol, cetyl alcohol, stearyl alcohol, isostearyl alcohol, oleyl alcohol, palmitoleyl alcohol, linoleyl alcohol, elaidyl alcohol, elaidolinoleyl alcohol, linolenyl alcohol, elaidolinolenyl alcohol, glycerine, glyceryl triacetate, sorbitol, xylitol, maltitol, polydextrose, quillaia, lactic acid, urea, and combinations thereof.

In one embodiment of the invention, the fatty alcohols are oleyl alcohol and lanolin alcohol with combined concentration of about 10% to 35%, or alternatively about 18% to about 24% by weight. More specifically, oleyl alcohol is present in the formula at a level of about 5% to 15% by weight (e.g. about 10% by weight). Lanolin alcohol is present in the formula at a level of about 3% to about 15% by weight, or alternatively from about 5% to 10% by weight (e.g. about 8% by weight).

Sorbitan tristearate is available commercially as Glycomul® TS (Lonza, Inc.) or SPAN 65 as sold by Merck Schuchardt OHG. Sorbitan tristearate is a low HLB ester based surfactant and has many uses in the food and cosmetic industries. The chemical structure of sorbitan tristearate is defined by a cyclic five member ether, with hydroxyl groups, and three fatty acid side chains. Sorbitan tristearate is present in the formula at a level of about 0.1% to 3% by weight, e.g. about 0.5% by weight.

Silicone Compound

After ivermectin has been pre-dissolved and stabilized by surfactants, a silicone compound may be added. In one embodiment, the silicone compound is selected from a group consisting of volatile silicones, of which cyclomethicone is one. Cyclomethicone may act as a conditioner in the shampoo-conditioner. It gives a soft, silky feel to hair and evaporates quickly leaving little residue. Cyclomethicone is present in the formula at a level of about 1% to 5% by weight, e.g. about 3% by weight. Thus, conditioners which may be used include but are in no way limited to cyclomethicone, dimethicone, hexamethyldisiloxane, octamethyltrisiloxane, decamethyltetrasiloxane, dodecamethylpentasiloxane, polydimethylsiloxanes and combinations thereof.

Preservatives

In yet another embodiment, the formula of the instant invention further contains a preservative, protecting the formula from fungus by chemicals. In one embodiment, the preservative is chosen from the paraben family. More specifically, the preservative is selected from methylparaben, propylparaben, or a combination thereof. In one embodiment, the concentration of the preservative is about 1% by weight. More specifically, methylparaben is present in the formula at levels of about 0.01% to 2% by weight (e.g. 0.20% by weight). Propylparaben is present in the formula at levels of about 0.01% to 1.0%, or alternatively from about 0.01% to about 0.5% by weight (e.g., 0.05% by weight). Also note that representative preservatives may include, but are not limited to, methylparaben, propylparaben, ethylparaben, butylparaben, isobutylparaben, isopropylparaben, benzylparaben and their sodium salts thereof.

Water

The oil mixture containing pre-dissolved ivermectin, suspending agents, surfactants, a silicone compound and preservatives is then dispersed in water. In one embodiment, water is deionized. Water acts as a carrier and may be included as warranted for any respective formulation. In the exemplified formulation, water is present in the formula at a level of about 30% to 40% by weight (e.g. 33% by weight). The addition of the oily mixture with ivermectin to deionized water results in a colloidal suspension of ivermectin, where micelles form around the ivermectin and are arranged such that hydrophilic heads of the surfactants are in contact with the solvent water molecules and the hydrophobic tails of the surfactants are in contact with ivermectin. This formulation is especially suitable delivering ivermectin in a shampoo-conditioner, which gives the shampoo-conditioner a suitable washout and flow behavior leaving the hair in good condition.

Specific ivermectin concentrations tested, as shown in Example 1, include 0.25%, 0.50% and 1.00% ivermectin. This concentration range, shown in Example 1 to effectively kill permethrin-resistant head lice, is presented to simply exemplify the invention and in no way limit the effective range that may be utilized by the artisan to practice the claimed invention. As noted above in this Detailed Description of the Invention section, the artisan may choose an appropriate range of ivermectin (measured as weight/volume [w/v]) anywhere in the range from about 0.005% to about 5%.

Of course, the w/v ratio of the formulation may be adjusted to take into account differing amounts of ivermectin on a g/l basis. Adjustments may easily be incorporated with components, known equivalent components, combination of components, and respective concentrations to provide for alternative avermectin- or ivermectin-based formulations for uses disclosed herein.

Thus, the artisan will be aware that the percentage by weight of any component may be adjusted to compensate for the concentration of the active ingredient, the texture of the topical formulation (e.g., shampoo, cream, gel) and that components may be added at differing concentrations or may be left out of a formulation or substituted with an equivalent component so as to provide for an avermectin- or ivermectin-based topical formulation which possesses efficacy against treatment-resistant strains of head, pubic or body lice similar to the exemplified topical formulation described herein.

TABLE 1

| Ingredient | % (by weight) |
| --- | --- |
| Ivermectin | 0.5 |
| Deionized Water | 33 |
| Olive Oil USP | 27.75 |
| Polysorbate 80 (and) | 11.75 |
| Cetyl Acetate (and) | 3.0 |
| Acetylated Lanolin Alcohol | .25 |
| Oleyl Alcohol | 10 |
| Lanolin Alcohol | 8 |
| Cyclomethicone | 3 |
| Shea Butter | 2 |
| Sorbitan Tristearate | 0.5 |
| Methylparaben | 0.2 |
| Propylparaben | 0.05 |

A person of the ordinary skill in the art will appreciate that other beneficial agents can be added into a formula of the instant invention. Such beneficial agents include, without limitation, vitamins, hair dyes, nutrients, anti-dandruff agents and the like.

A person of the ordinary skill will have sufficient expertise to properly select the beneficial agent or the combination thereof depending on the specific embodiment of the invention, so that the at least one beneficial agent would not negate the beneficial aspects of the formula.

One of ordinary skill in the art would appreciate that the formulation and method described herein for eliminating treatment resistant lice is not meant to be a limiting disclosure, but only gives a preferred embodiment of the invention.

EXAMPLE 1

Formulation and Testing of Ivermectin Shampoo-conditioner on Permethrin Resistant Head Lice Having described the invention in general terms, the following specific example is offered for purposes of illustration and for illustration only, and no intention to limit the invention is to be inferred therefrom. A pediculicide containing ivermectin as a topical shampoo-conditioner for eliminating treatment resistant lice may be prepared as follows.

Preparing the Formulation

The formulation shown in Table 1 may be made by the following non-limiting example. The 0.50% w/v of the active ingredient (ivermectin) is pre-dissolved in a vessel containing surfactants, hereinafter Phase A, consisting of 11.75% w/v of polysorbate 80, 3% w/v of cetyl acetate, and 0.25% w/v of acetylated lanolin alcohol. Phase A is heated, with mixing, at a constant temperature of 65° C. until the active ingredient is completely dissolved in the surfactants. Phase A is then transferred into a vessel containing Phase B, wherein Phase B consists of suspending agents, preservatives, non-ionic surfactants, humectants, and a conditioner agent.

Phase B may consist of 27.75% w/v of olive oil, 2% w/v of shea butter, 8% w/v of lanolin alcohol, 3% w/v of cyclomethicone, 0.50% w/v of sorbitan triesterate, 0.20% w/v of methyl paraben, and 0.05% w/v of propyl paraben. Phase B combined with Phase A are heated, with mixing, at a constant temperature of about 85° C. until all ingredients are dissolved and/or melted. Concurrently, Phase C, consisting of water, is heated at a constant temperature of about 85° C. With vigorous mixing, Phase A/B is slowly transferred into Phase C. Continue mixing the formulation at or near room temperature until the desired formulation consistency is obtained and subsequently package the formulation.

Formulated Ivermectin Concentrations

The present invention may be prepared in concentrations of 1%, 0.5%, and 0.25% of ivermectin in a formulation containing deionized water, olive oil USP, surfactants, shea butter, sorbitan tristearate, methylparaben, and propylparaben. For comparison purposes, a Nix® formulation (Pfizer, Morris Plains, N.J.) containing 1% permethrin (v/v), an Ovide® formulation (Medicis, Phoenix, Ariz.) containing 0.5% malathion (v/v), a non-formulated ivermectin solution (Chem Service Inc., West Chester, Pa.), a placebo formulation (ivermectin formulation sans ivermectin) and distilled, deionized water (ddH$_2$O) are used as positive (Nix®, Ovide® and non-formulated ivermectin), negative (placebo), and no treatment (ddH2O) controls.

Selection of Human Head Lice

The SF-HL strain of permethrin-resistant human head lice (*Pediculus humanus* capitis, Phthiraptera:Pediculidae) is collected from infested children in Plantation and Homestead, Fla. and is maintained on an in vitro feeding system at the University of Massachusetts at Amherst, Mass. as described by Yoon et al. (2006). Lice are maintained without a human host on the in vitro rearing system from about 24 to about 36 generations. Permethrin-resistant SF-HL are selected periodically using 1% permethrin-treated filter papers (Yoon et al. 2006). Filter papers (35 mm diameter, Whatman No. 1) are immersed into 1% permethrin dissolved in acetone (w/v) for 10 seconds and is air dried in a dark fumehood from about 20 to about 30 minutes. Mixed developmental stages (first instars to adult) are placed on the treated filter paper and exposed for about 5 hours. Surviving lice are transferred back into the feeding system. The SF-HL strain are susceptible to Ovide® (0.5% malathion), but resistant to Nix® (1% permethirn) and cross-resistant to DDT treatments. (Yoon et al. 2003).

Bioassays

Mortality bioassays are performed to compare lethal time to 50% mortality values ($LT_{50}$) between the ivermectin formulations, Nix®, and Ovide®. Experimental lice are newly hatched first instars (less than 24 hours old). The lice are randomly taken from the in vitro rearing system, where the lice take an overnight blood meal. Lice (about 30 lice/treatment) are placed on an individual hair tuft (about 300 strands, about 4 cm in length) using sterile forceps, and the treatment is gently rubbed into the hair until saturation occurs.

After a 10 minute exposure period, the hair tuft with lice are washed sequentially in three separate water baths, containing about 10 ml of ddH2O for about 5 seconds each. The washed hair tuft with lice is blotted onto stacks of filter paper and air dried for about 5 minutes. Any lice dislodged during treatment or washing are placed back onto the treated hair tuft. After drying, the treated hair tuft with lice is examined under a dissecting microscope and the number of dead lice is recorded.

A louse is considered dead if it can not right itself when inverted and when its legs have ceased all movements when probed. Treated hair tufts with lice are then placed onto the feeding membrane in the in vitro rearing system and are maintained at 31° C. and 75% humidity. The numbers of dead lice are reassessed at 10 minute intervals until a greater than 90% mortality is achieved. The timing for mortality begins immediately following the 10 minute exposure period. Because of this, mortality is not assessed during the washing and drying intervals (about 5 minutes). Log time versus logit percent mortality regression lines are generated to determine $LT_{50}$ and $LT_{95}$ values and maximum log-likelihood ratio tests are performed to test the equality (slope and intercept) of the regression lines (p<0.05, Polo PC, LeOra Software, 1987).

To determine whether ivermectin in formulation performs better than ivermectin alone, blood-fed lice are placed onto 0.5% (w/v) ivermectin formulation-treated hair tufts as described above. Blood-fed lice are also placed onto hair tufts that are treated with 0.5% ivermectin in acetone (acetone is allowed to volatilize in a fumehood for about 1 hour prior to transferring lice to the treated hair tuft), washed, and transferred to the in vitro rearing system as described above.

SF-HL Lice Mortality Response to Ivermectin Formulations

Figure 3:
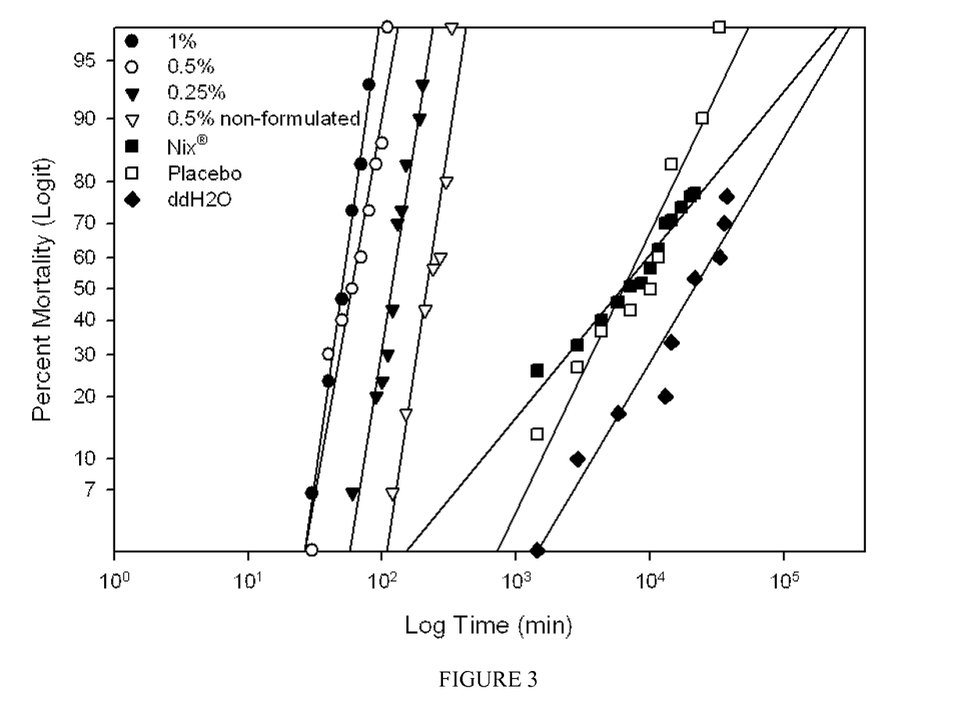
FIG. 3 shows log time versus percent mortality of permethrin-resistant human head lice from the South Florida (SF-HL) strain following a 10 minute exposure to 1%, 0.5%, and 0.25% ivermectin formulations.
Figure 4:
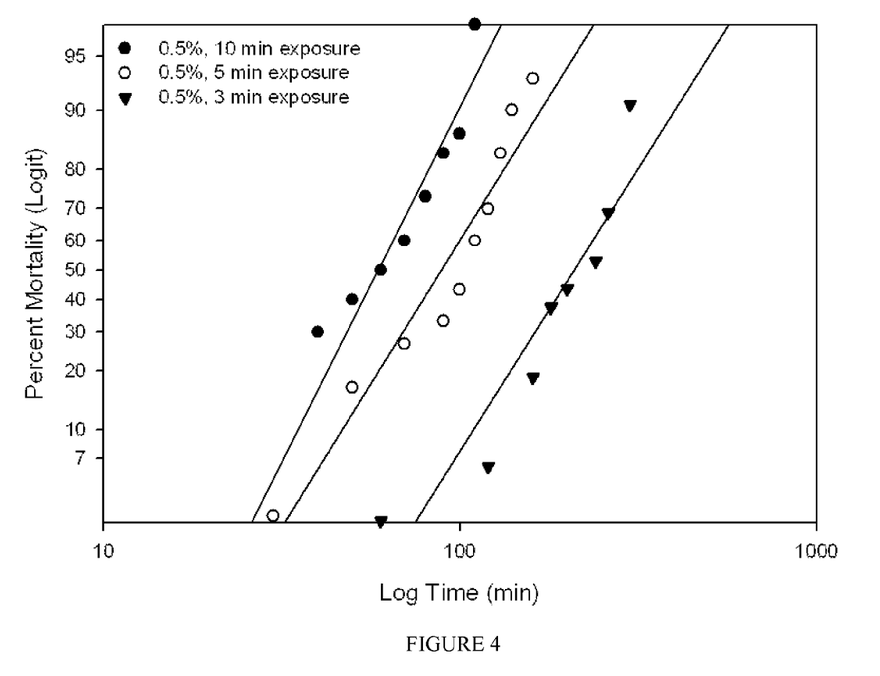
FIG. 4 shows log time versus percent mortality of permethrin-resistant human head lice from the South Florida (SF-HL) strain treated with a 0.5% ivermectin formulation for 3 minutes, 5 minutes, and 10 minutes.

The mortality responses of the SF-HL lice strain following a 10 minute exposure to all three ivermectin formulations (1%, 0.5%, and 0.25%) are significantly different compared to SF-HL lice exposed only to ddH2O ($x^2$=90.1, df=2, P<0.001; $x^2$=199.5, df=2, P<0.001, $x^2$=213.5, df=2, P<0.001), respectively (FIG. 3). At the $LT_{50}$ and $LT_{95}$ following a 10 minute exposure, the 1% ivermectin formulation is 426 and 491 times faster than the ddH2O treatments, respectively (Table 2).

TABLE 2

Comparison of median lethal time ($LT_{50}$ and $LT_{95}$, following exposures of the SF-HL lice strain to the ivermectin formulations).

| Treatment | $LT_{50}$ (CL)[a] | $LT_{95}$ (CL)[a] | Slope | Reject null hypothesis[b] |
|---|---|---|---|---|
| 1% | 50.4 (46.5-54.1) | 88.0 (78.7-104.5) | 12.1 ± 1.7 | + |
| 0.5% | 58.1 (52.9-63.0) | 130.4 (113.8-158.7) | 8.4 ± 1.0 | + |
| 0.5% (5 min exposure) | 93.7 (82.9-103.6) | 196.7 (168.8-249.1) | 8.5 ± 1.1 | + |
| 0.5% (3 min exposure) | 204.7 (176.7-236.8) | 426.4 (359.3-556.7) | 10.5 ± 1.5 | + |
| 0.25% | 119.3 (112.7-125.9) | 208.9 (189.2-241.5) | 12.1 ± 1.5 | + |
| 0.5% (non-formulated) | 221.8 (204.5-238.5) | 419.4 (363.9-532.5) | 10.6 ± 1.5 | + |
| Placebo (formulation sans ivermectin) | 4.8 days (3.6-6.2) | 24 days | 3.3 ± 0.4 | + |
| Nix ®[c] | 4.3 days (3.9-4.8) | >15 days | 2.1 ± 0.17 | + |
| Nix ® (EC-HL)[d] | 177.7 (126.1-223.3) | 357.0 (282.7-628.6) | 9.7 ± 1.8 | + |
| $ddH_2O$ | 14.9 days (12.0-18.8) | 30 days | 3.1 ± 0.5 | + |
| Ovide ®[e] | <5.0 | <5.0 | — | + |

Slope values are determined from log time versus logit mortality regression lines, which are obtained using the hair tuft bioassay of the permethrin-resistant (SF-HL) and permethrin-susceptible (EC-HL) head louse populations.
Populations are treated with the formulations, Nix ®, and Ovide ®.
[a] CL, 95% confidence interval limit.
[b] The null hypothesis tests for equality of the slope and intercept of the regressions (p < 0.05) (see maximum log-likelihood ratio test in text).
[c] Nix ® $LT_{50}$ values for SF-HL and EC-HL are from historical data previously determined using the same experimental bioassay (Yoon et al. 2006).
[d] EC-HL are permethrin-susceptible lice collected from Kuna Indians in Ecuador.
[e] $LT_{50}$ and $LT_{95}$ values following Ovide ® treatments are estimated times since log time versus logit mortality responses curves were not generated given the fast response times (see methods section).

At the $LT_{50}$ and $LT_{95}$ following a 10 minute exposure, the 0.5% ivermectin formulation is 369 and 331 times faster than the $ddH_2O$ treatments, respectively, and the 0.25% ivermectin formulation is 180 and 207 times faster than the ddH2O treatments, respectively (Table 2). The mortality response to the non-formulated 0.5% ivermectin treatment is significantly different compared to ddH2O ($x^2=168.1$, df=2, P<0.001) (FIG. 1). At the $LT_{50}$ and $LT_{95}$ following a 10 minute exposure, non-formulated 0.5% ivermectin is 96.7 and 103.0 times faster than ddH2O treatment, respectively (Table 2).

Ivermectin as Compared to Placebo

The mortality responses for all three of the ivermectin formulations are significantly different compared to the placebo formulation ($x^2=157.5$, df=2, P<0.001; $x^2=178.8$, df=2, P<0.001; $x^2=190.0$, df=2, P<0.001, respectively). At the $LT_{50}$ and $LT_{95}$ following a 10 minute exposure, the 1% ivermectin formulation is 137 and 393 times faster than placebo formulation, respectively (Table 2). At the $LT_{50}$ and $LT_{95}$ following a 10 minute exposure, the 0.5% ivermectin formulation is 119 and 265 times faster than the placebo formulation, respectively. At the $LT_{50}$ and $LT_{95}$ following a 10 minute exposure, the 0.25% ivermectin formulation is 58 and 165 times faster than the placebo formulation, respectively (Table 2).

The mortality response to non-formulated 0.5% ivermectin is significantly different compared to the placebo formulation ($x^2=143.8$ df=2, P<0.001). At the $LT_{50}$ and $LT_{95}$ following a 10 minute exposure, non-formulated 0.5% ivermectin is 31.2 and 82.4 times faster than placebo treatment, respectively (Table 2).

Ivermectin as Compared to Nix®

The mortality responses for all three of the ivermectin formulations are significantly different compared to the Nix® ($x^2=211.8$, df=2, P<0.001; $x^2=244.0$, df=2, P<0.001; $x^2=244.0$, df=2, P<0.001), respectively (FIG. 3). At the $LT_{50}$ and $LT_{95}$ following a 10 minute exposure, the 1% ivermectin formulation is 123 and 245 times faster than Nix®, respectively (Table 2). At the $LT_{50}$ and $LT_{95}$ following a 10 minute exposure, the 0.5% ivermectin formulation is 107 and 166 times faster than Nix®, respectively. At the $LT_{50}$ and $LT_{95}$ following a 10 minute exposure, the 0.25% ivermectin formulation is 52 and 103 times faster than Nix®, respectively (Table 2). The mortality response to non-formulated 0.5% ivermectin is significantly different compared to Nix® ($x^2=180.6$ df=2, P<0.001). At the $LT_{50}$ and $LT_{95}$ following a 10 minute exposure, non-formulated 0.5% ivermectin is 27.9 and 51.5 times faster than Nix®, respectively (Table 2).

The mortality responses for all three of the ivermectin formulations are significantly different compared to non-formulated 0.5% ivermectin ($x^2=143.8$, df=2, P<0.001; $x^2=153.2$, df=2, P<0.001; $x^2=100.3$, df=2, P<0.001, respectively) (FIG. 3). At the $LT_{50}$ and $LT_{95}$ following a 10 minute exposure, the 1% ivermectin formulation is 4.4 and 4.8 times faster than non-formulated 0.5% ivermectin (Table 2). At the $LT_{50}$ and $LT_{95}$ following a 10 minute exposure, the 0.5% ivermectin formulation is 3.8 and 3.2 times faster than the 0.5% non-formulated ivermectin, respectively. At the $LT_{50}$ and $LT_{95}$ following a 10 minute exposure, the 0.25% ivermectin formulation is 1.9 and 2.0 times faster than non-formulated 0.5% ivermectin, respectively (Table 2).

Mortality Response of 1% Ivermectin Formulation as Compared to 0.5% and 0.25% Ivermectin Formulations The mortality response for the 1% ivermectin formulation is significantly different from that produced by the 0.5% and the 0.25% formulations following 10 minute exposures ($x^2=11.5$, df=2, P=0.003, $x^2=134.8$, df=2, P=0.001, respectively) (FIG. 3). At the $LT_{50}$ and $LT_{95}$ following a 10 minute exposure, the 1% ivermectin formulation is 1.2 and 1.5 times faster than the 0.5% ivermectin formulation, respectively (Table 1). At the $LT_{50}$ and $LT_{95}$ following a 10 minute exposure, the 1% ivermectin formulation is 2.4 and 2.4 times faster than the 0.25% ivermectin formulation, respectively (Table 2).

The mortality response for the 0.5% ivermectin formulation is significantly different than that produced by the 0.25% formulation following a 10 minute exposure ($x^2=121.5$, df=2, P<0.001) (FIG. 1). At the $LT_{50}$ and $LT_{95}$ following a 10 minute exposure, the 0.5% ivermectin formulation is 2.0 and 1.6 times faster than the 0.25% ivermectin formulation, respectively (Table 2).

Mortality Response Following 5 and 3 Minute Exposure of the 1% and 0.5% Ivermectin Formulations The mortality response for the 1% ivermectin formulation following a 10 minute exposure is significantly different compared to the 0.5% ivermectin formulation with a 5 minute exposure and the 0.5% ivermectin formulation with a 3 minute exposure ($x^2=80.6$, df=2, P<0.001, $X^2=163.3$, df=2, P<0.001), respectively. At the $LT_{50}$ and $LT_{95}$, the 1.0% ivermectin formulation following a 10 minute exposure is 1.9 and 2.2 times faster than the 0.5% ivermectin formulation with a 5 minute exposure, respectively (Table 2).

At the $LT_{50}$ and $LT_{95}$, the 1.0% ivermectin formulation following a 10 minute exposure is 4.1 and 4.9 times faster than the 0.5% ivermectin formulation with a 3 minute exposure, respectively (Table 2). The mortality response for the 0.5% ivermectin formulation following a 10 minute exposure is significantly different compared to the 0.5% formulation with a 5 minute exposure and the 0.5% ivermectin formulation with a 3 minute exposure ($x^2=55.1$, df=2, P<0.001, $x^2=175.2$, df=2, P<0.001), respectively. At the $LT_{50}$ and $LT_{95}$, the 0.5% ivermectin formulation with a 10 minute exposure is 1.6 and 1.5 times faster than the 0.5% ivermectin formulation with a 5 minute exposure, respectively (Table 2). At the $LT_{50}$ and $LT_{95}$, the 0.5% ivermectin formulation following a 5 minute exposure is 3.5 and 3.3 times faster than the 0.5% ivermectin formulation with a 3 minute exposure, respectively (Table 2).

The mortality response for the 0.25% ivermectin formulation following a 10 minute exposure is significantly different from that produced by the 0.5% formulation with a 5 minute exposure and the 0.5% ivermectin formulation with a 3 minute exposure ($x^2=25.6$, df=2, P<0.001, $x^2=95.0$, df=2, P<0.001), respectively (FIG. 3). At the $LT_{50}$ and $LT_{95}$, the 0.25% ivermectin formulation following a 10 minute exposure is 1.3 and 1.1 times slower than the 0.5% ivermectin formulation with a 5 minute exposure, respectively (Table 2). At the $LT_{50}$ and $LT_{95}$, the 0.25% ivermectin formulation following a 10 minute exposure is 1.7 and 2.0 times faster than the 0.5% formulation with a 3 minute exposure, respectively (Table 2).

The mortality response for the 0.5% formulation with a minute exposure is significantly different compared to the 0.5% formulation with a 3 minute exposure ($x^2=118.8$, df=2, P<0.001). At the $LT_{50}$ and $LT_{95}$, the 0.5% formulation with a 5 min exposure is 2.2 and 2.2 times faster than the 0.5% formulation with a 3 min exposure, respectively (Table 1).

Ivermectin Formulation Results Summary

Treatments with 1%, 0.5% and 0.25% ivermectin formulations result in a significantly faster mortality response than treatments with placebo or ddH2O, indicating that the present invention is pediculicidal on permethrin-resistant head lice. Ivermectin formulations have a faster mortality response than Nix® treatments indicating that the ivermectin formulation of the present invention is a faster acting pediculicide. The 1% ivermectin formulation works significantly faster than its 0.5% formulation and the 0.5% formulation works significantly faster than its 0.25% formulation.

The 0.5% ivermectin formulation with a 10 minute exposure works significantly faster than the 0.5% formulation with a 5 minute exposure and both are significantly faster than the 0.5% formulation with a 3 minute exposure.

However, the non-formulated 0.5% ivermectin solution is 3.2 to 3.8 times slower at killing SF-HL than the 0.5% ivermectin formulation of the present invention. The exact reason for the superior killing power of ivermectin in formulation may be due to the increased penetration, or increased transfer, of the active ingredient residues to louse cuticles.

Nix® is not 100% effective at killing treated SF-HL using the hair tuft bioassay system (Yoon et al. 2006). All ivermectin formulations disclosed herein kills 100% of SF-HL lice.

Development of Lice on Substrates Treated with Ivermectin

A nit of head lice normally undergoes a 7-9 day incubation before hatching as a baby nymph. It looks like an adult head louse, but is smaller. Nymphs mature into adults about 7 days after hatching. To live, the nymph must feed on blood. It metamorphoses 3 times before it reaches the adult stage.

During the experiments, including those described above, it was observed that the eggs incubated on substrates treated with the compositions of the instant invention were able to hatch into first instar nymphs but then all died. It is indirectly ovicidal. This mode of action is different from the mode of action of permethrin. It was also observed that but the nymphs died almost immediately after hatching. Therefore, these observations demonstrate that the compositions of the instant penetrates the egg and the invention are efficient at least for 7-9 days (i.e., the time needed for incubation of the eggs)

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for the treatment or prophylaxis of lice infestation, the method comprising steps of:
  a) applying topically to a surface area of a host who is suffering from or susceptible to infestation with lice a formulation comprising:
    an effective amount of dissolved ivermectin;
    about 20% to about 35% by weight olive oil;
    about 1% to about 5% by weight shea butter;
    nonionic surfactants comprising oleyl alcohol, sorbitan tristearate, and lanolin alcohol;
    a solubilizing agent comprising cetyl acetate, polysorbate 80, and acetylated lanolin alcohol;
    about 0.01% to about 2% by weight methylparaben;
    about 0.01% to about 0.5% by weight propylparaben;
    about 1% to about 5% by weight of a conditioner comprising cyclomethicone; and
    about 30% to about 40% by weight water; and
  b) maintaining the composition in contact with the surface area for a period of time that is from about 1 to about 60 minutes in length.

2. The method of claim 1, further comprising a step of:
  c) washing the area with water.

3. The method of claim 1, wherein the lice are head lice and the surface area comprises head hair of the host.

4. The method of claim 1, wherein the lice are body lice and the surface area comprises a body area of the host.

5. The method of claim 1, wherein the lice are pubic lice and the surface area comprises a pubic area, facial hair, eyelashes, eyebrows, armpits, chest hair, or scalp of the host.

6. The method of claim 1, wherein the lice are resistant to one or more of pyrethrin, permethrin and malathion.

7. The method of claim 1, wherein the step of applying comprises applying to a host who has previously used one or more of a pyrethrin, permethrin and malathion containing formulation.

8. The method of claim 1, wherein the lice are susceptible to ivermectin.

9. The method of claim 1, wherein the step of applying comprises applying to a host who has not previously used one or more of a pyrethrin, permethrin and malathion containing formulation.

10. The method of claim 1, wherein the period of time is from about 3 minutes to about 60 minutes in length.

11. The method of claim 1, wherein the period of time is about 3 minutes in length.

12. The method of claim 1, wherein the period of time is about 5 minutes in length.

13. The method of claim 1, wherein the period of time is about 10 minutes in length.

14. The method of claim 1, wherein the formulation is in the form of a lotion.

15. The method of claim 1, wherein the step of applying comprises applying a unit dose of about 1 ml to about 100 ml of the formulation.

16. The method of claim 1, wherein the step of applying comprises applying a unit dose of about 3 ml to about 75 ml of the formulation.

17. The method of claim 15 or 16, wherein the unit dose comprises from about 0.1% to about 2.0% w/v ivermectin.

18. The method of claim 15 or 16, wherein the unit dose comprises about 0.5% w/v ivermectin.

19. The method of claim 1, wherein the formulation does not include any glycols.

20. The method of claim 1, wherein the formulation comprises below 5% by weight of a glycol.

21. The method of claim 1, wherein the olive oil is present in an amount of about 27.5% by weight of the formulation.

22. The method of claim 1, wherein the ivermectin is present in an amount of about 0.25% to about 1% by weight of the formulation.

23. The method of claim 1, wherein the formulation is formulated as a cream, gel, pomade, shampoo-conditioner, cream rinse or lotion.

24. The method of claim 23, wherein the formulation is formulated as a cream.

25. The method of claim 1, wherein the formulation is indirectly ovicidal.

26. The method of claim 1, wherein the formulation has a volume of about 1 mL to about 100 mL and contains a unit dose of ivermectin.

27. The method of claim 1, wherein the formulation comprises oleyl alcohol and lanolin alcohol with a combined concentration of about 10% to about 35% by weight.

28. The method of claim 1, wherein the formulation comprises oleyl alcohol and lanolin alcohol with a combined concentration of about 18% to about 24% by weight.

29. The method of claim 1, wherein the formulation comprises about 5% to about 15% by weight oleyl alcohol.

30. The method of claim 1, wherein the formulation comprises about 3% to about 15% by weight lanolin alcohol.

31. The method of claim 1, wherein the formulation comprises about 5% to about 10% by weight lanolin alcohol.

32. The method of claim 1, wherein the formulation comprises about 0.1% to about 3% by weight sorbitan tristearate.

33. The method of claim 1, wherein the formulation comprises about 0.5% to about 10% by weight cetyl acetate.

34. The method of claim 1, wherein the formulation comprises about 1% to about 4% by weight cetyl acetate.

35. The method of claim 1, wherein the formulation comprises about 5% to about 25% by weight polysorbate 80.

36. The method of claim 1, wherein the formulation comprises about 10% to about 15% by weight polysorbate 80.

37. The method of claim 1, wherein the formulation comprises about 0.10% to about 3% by weight acetylated lanolin alcohol.

38. The method of claim 1, wherein the formulation comprises about 0.5% to about 1% by weight acetylated lanolin alcohol.

39. The method of claim 1, wherein the ivermectin is present in an amount of about 0.05% to about 5% by weight of the formulation.

40. The method of claim 1, wherein the olive oil is present in an amount of about 20% to about 30% by weight of the formulation.

41. The method of claim 1, wherein the olive oil is present in an amount of about 25% to about 28% by weight of the formulation.

* * * * *